US012590972B2

(12) United States Patent
Fukuyama

(10) Patent No.: US 12,590,972 B2
(45) Date of Patent: Mar. 31, 2026

(54) METHOD FOR IDENTIFYING MARKER FOR DISCRIMINATING MICROORGANISM

(71) Applicant: SHIMADZU CORPORATION, Kyoto (JP)

(72) Inventor: Yuko Fukuyama, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 610 days.

(21) Appl. No.: 18/007,934

(22) PCT Filed: Jun. 2, 2020

(86) PCT No.: PCT/JP2020/021808
§ 371 (c)(1),
(2) Date: Dec. 2, 2022

(87) PCT Pub. No.: WO2021/245798
PCT Pub. Date: Dec. 9, 2021

(65) Prior Publication Data

US 2023/0243847 A1 Aug. 3, 2023

(51) Int. Cl.
*G01N 33/68* (2006.01)

(52) U.S. Cl.
CPC ... *G01N 33/6851* (2013.01); *G01N 2333/255* (2013.01)

(58) Field of Classification Search
CPC ......... G01N 33/6851; G01N 2333/255; G01N 2333/25; G16B 40/10; G16B 20/00; C12Q 1/04; Y02A 50/30
See application file for complete search history.

(56) References Cited

U.S. PATENT DOCUMENTS

2017/0355031 A1 12/2017 Metelsky et al.
2019/0056407 A1 2/2019 Tamura et al.
(Continued)

FOREIGN PATENT DOCUMENTS

JP 2015-184020 A 10/2015
JP WO2017/168740 A1 10/2017
(Continued)

OTHER PUBLICATIONS

Hiroto Tamura, "MALDI-TOF-MS Based on Ribosomal Protein Coding in S10-spc-alpha Operons for Proteotyping", MALDI-TOF and Tandem MS for Clinical Microbiology, Apr. 7, 2017, pp. 269-310 (42 pages).
(Continued)

*Primary Examiner* — Samuel P Siefke
(74) *Attorney, Agent, or Firm* — Sughrue Mion, PLLC

(57) ABSTRACT

[Problem to be solved] To provide a method for identifying a marker for discriminating a microorganism based on a small amount of actual measurement data.
[Solution] A method for identifying a marker for discriminating a microorganism, including steps of:
Step 1: Selecting a microorganism whose entire genome has been decoded,
Step 2: Obtaining molecular weight-related ion peaks of a protein of the microorganism,
Step 3: Obtaining an actual m/z value of each peak from the molecular weight-related ion peaks,
Step 4: Calculating a theoretical m/z value of the protein present in the microorganism,
Step 5: Comparing the theoretical m/z value with the actual m/z value, and assign the actual m/z value to a protein and an amino acid sequence thereof that have theoretical m/z values that match the actual m/z values,
Step 6: Obtaining an amino acid sequence similar to the protein assigned in Step 5 above,
(Continued)

A flow chart of a method for identifying a marker used for discriminating a microorganism Step 7: Calculating the theoretical m/z value of the protein of the microorganism selected according to discrimination and classification, and Step 8: Comparing the theoretical m/z values of the above protein and identify the theoretical m/z value with difference as a marker for discrimination.

6 Claims, 2 Drawing Sheets

(56) References Cited

U.S. PATENT DOCUMENTS

| | | | |
|---|---|---|---|
| 2019/0242903 | A1 | 8/2019 | Tamura et al. |
| 2020/0300862 | A1 | 9/2020 | Tamura et al. |

FOREIGN PATENT DOCUMENTS

| | | | |
|---|---|---|---|
| JP | WO2017/168742 | A1 | 10/2017 |
| JP | WO2017/168743 | A1 | 10/2017 |
| JP | 2018-505063 | A | 2/2018 |

OTHER PUBLICATIONS

Ralf Dieckmann, et al."Rapid Classification and Identification of *Salmonellae* at the Species and Subspecies Levels by Whole-Cell Matrix-Assisted Laser Desorption Ionization-Time of Flight Mass Spectrometry" Applied and Environmental Microbiology, Dec. 15, 2008, vol. 74, No. 24, pp. 7767-7778 (12 pages).

Extended European Search Report dated Jan. 23, 2024 in Application No. 20939271.1.

Teruyo Ojima-Kato et al., "Application of proteotyping strain solution TM ver. 2 software and theoretically calculated mass database in MALDI-TOF MS typing of *Salmonella* serotype", Applied Microbial and Cell Physiology, Oct. 14, 2017, vol. 101, pp. 8561-8568.

International Search Report for PCT/JP2020/021808 dated Aug. 18, 2020.

Chinese Office Action issued Mar. 7, 2024 in Application No. 2020801015811.

Japanese Office Action issued May 30, 2023 in Application No. 2022-529184.

Step 1 : Select a microorganism whose entire genome has been decoded.

Step 2 : Perform mass spectrometry on a protein possessed by the microorganism selected in Step 1 above to obtain molecular weight-related ion peaks.

Step 3 : Obtain a m/z value of each peak is obtained as an actual measurement value from the molecular weight-related ion peaks obtained in Step 2 above (hereinafter, may be referred to as "actual m/z value").

Step 4 : Obtain information of the protein possessed by the microorganism and an amino acid sequence thereof from a genetic database and obtain a theoretical m/z value of the protein from the information of the amino acid sequence.

Step 5 : Compare the theoretical m/z value with the actual m/z value and assign the actual m/z value to a protein and an amino acid sequence thereof that have theoretical m/z values that match the actual m/z values.

Step 6 : Obtain amino acid sequences similar to the assigned protein from the database.

Step 7 : Among microorganisms having similar amino acid sequences, select a microorganism according to discrimination and classification, and calculate the theoretical m/z value of the amino acid sequence of the protein possessed by the microorganism.

Step 8 : Compare the theoretical m/z values of the amino acid sequence calculated in Step 7 for each classification, and identify the protein with different theoretical m/z values for each classification as a marker for discrimination.

FIG. 1 A flow chart of a method for identifying a marker used for discriminating a microorganism

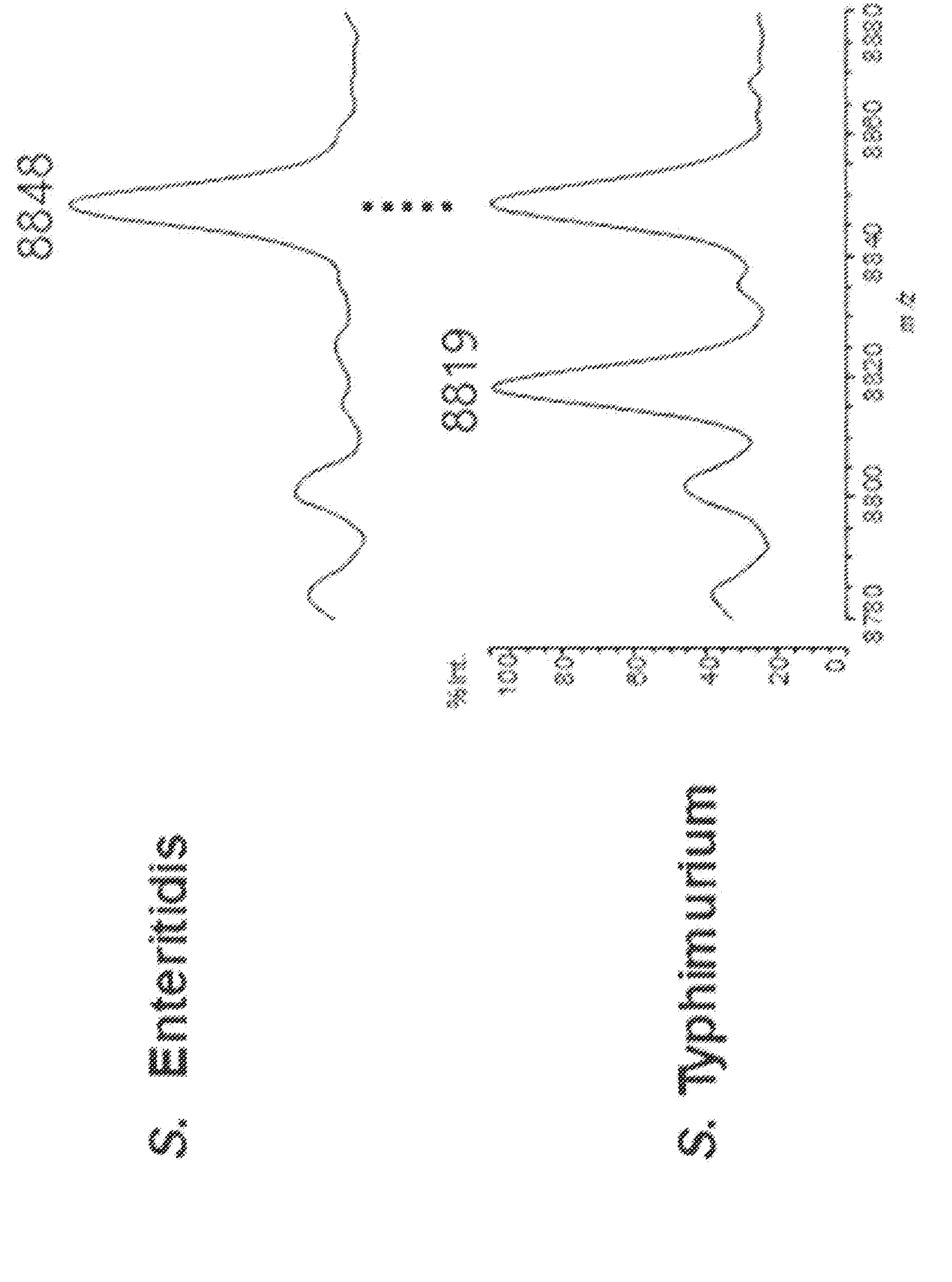
FIG. 2 Mass spectra of ChaB in S. Enteritidis and S. Typhimuriu

METHOD FOR IDENTIFYING MARKER FOR DISCRIMINATING MICROORGANISM

This Application is a National Stage of International Application No. PCT/JP2020/021808 filed Jun. 2, 2020.

TECHNICAL FIELD

The present invention relates to a method for identifying a marker used for discriminating a microorganism. More particularly, the present invention relates to a method for identifying a marker for discriminating a microorganism using mass spectrometry.

RELATED ART

Conventionally, homology analysis based on DNA base sequences has been widely used as one of methods for identifying types of microorganisms. Such techniques using DNA base sequences require a relatively long time to extract DNA from a microorganism to be discriminated and to determine DNA base sequences.

However, when infected with bacteria that cause various diseases, it is extremely important to identify the bacteria rapidly and accurately for the prevention of secondary infections as well as the cure of the patient. Therefore, there is a need for a rapid and accurate method for analyzing bacteria.

Therefore, in recent years, a method has been used to identify microorganisms based on mass spectral patterns obtained by mass spectrometry of microorganisms to be discriminated. According to mass spectrometry, analysis results can be obtained in a short period of time using a very small amount of a microbial sample, and continuous analysis of many specimens can be easily performed, so simple and rapid identification of microorganisms is possible. In particular, since a soft ionization method, which ionizes biopolymers such as proteins without decomposing them as much as possible, has been put into practical use, mass spectrometry has been widely applied to the analysis of microorganisms.

Among the soft ionization methods, mass spectrometry using an ionization method called matrix-assisted laser desorption ionization mass spectrometry (hereinafter, may be referred to as "MALDI-MS") has recently attracted attention as a means of analyzing microorganisms. A microorganism to be discriminated is identified by collating the mass spectral pattern obtained by MALDI-MS with the mass spectral patterns of known microorganisms preliminarily stored in a database. Such a method is called a fingerprinting method because it uses the mass spectral pattern as information (that is, a fingerprint) specific to each microorganism.

In the identification of microorganisms using MALDI-MS, the fingerprint method is known for analysis up to species, and has been put into practical use in some clinical fields. On the other hand, for analysis of subspecies and serotypes, for example, Patent Document 1 reports a method using ribosomal proteins or the like as markers. In the method of Patent Document 1, the detected peak information (m/z value, etc.) of the mass spectrum measured in advance is queried with the measured data of the analyte, and microorganisms are discriminated by the presence or absence of peaks with specific m/z values assigned to the markers.

Patent Document 2 describes a method of comparing data of each group in a plurality of groups composed of a plurality of data, performing differential analysis, and searching for markers for identifying each group.

Furthermore, results of identifying markers and discriminating microorganisms using the methods of Patent Documents 1 and 2 above have also been obtained.

For example, for *Salmonella enterica* subsp. *enterica* of the genus *Salmonella*, a method has been reported in which species are identified by a fingerprint method and serotypes are identified using 12 markers (Patent Document 3, Non Patent document 1).

According to Non-Patent Document 1, according to the method of Patent Document 1, by referring to the detected peak information of the mass spectrum measured in advance such as the m/z value with the actual data, so that the microorganisms to be discriminated are identified to be of the genus *Salmonella*. Next, data from multiple strains grouped by serotype are then compared to identify markers that identify each serotype. It is reported that 12 types of *Salmonella* serotype discrimination markers were identified by such a method, and that 22 types of serotypes can be discriminated by these markers.

PRIOR ART DOCUMENT

Patent Document

Patent Document 1: JP-A 2015-184020
Patent Document 2: JP-A 2018-505063
Patent Document 2: WO 2017/168740 A

Non-Patent Document

Non-Patent Document 1: Applied Microbiology and Biotechnology, 2017, Vol. 101, No. 23-24, pp. 8557-8569.

SUMMARY OF THE INVENTION

Problem to be Solved by the Invention

It is known that microorganisms, even if they belong to the same genus, are finely classified into species, subspecies, serotypes, strains, etc., and have different properties. For example, in the case of the above-mentioned *Salmonella* genus, there are two species, *enterica* and *bongori*, or three species including *subterranea* in addition to *enterica* and *bongori*, and *enterica* has six subspecies. Furthermore, each subspecies has different serotypes and strains, and for example, subspecies *enterica* is said to have more than 2000 serotypes.

In addition, some microorganisms are pathogenic to humans while others are not, and serotypes have different biological properties. Therefore, there is a need to discriminate subspecies, serotypes, and strains of microorganisms by a simple and rapid method.

Since there are many serotypes and strains of microorganisms, it is not easy to analyze all of them. In addition, in the analysis of microorganisms pathogenic to humans, it is important to reduce the number of actual measurements as much as possible from the viewpoint of the safety of the inspector. Furthermore, the types of samples that can be purchased are limited. Therefore, there is a limit to marker search based only on measured data as in the above method. Therefore, the number of markers reported so far is limited, and the species, subspecies, and serotypes that can be discriminated by the markers are also limited.

In addition, in the case of microorganisms with a huge number of serotypes and strains, there is little actual measurement data that can be used for discrimination, and a database of actual measurement data has not yet been fully developed.

Therefore, a method for identifying markers for discriminating microorganisms based on as little actual measurement data as possible has been desired.

Means for Solving the Problem

The present inventors studied a method of searching for a marker that can discriminate genus, species, subspecies, and serotype of microorganisms to be discriminated from the analysis results obtained by mass spectrometry and available public genetic information. The present inventors have found a method for identifying a marker based on as little actual measurement data as possible and have arrived at the present invention.

That is, the present invention relates to a method for identifying a marker for discriminating a microorganism, including steps 1 to 8 below.

Step 1: Select a microorganism whose entire genome has been decoded.

Step 2: Perform mass spectrometry on protein possessed by the microorganism selected in Step 1 above to obtain molecular weight-related ion peaks of the protein.

Step 3: Obtain an actual m/z value of each peak from the molecular weight-related ion peaks obtained in Step 2 above.

Step 4: For the microorganism selected in Step 1 above, obtain information of the protein possessed by the microorganism and an amino acid sequence thereof from a genetic database, and calculate a theoretical m/z value of the protein from the information of the amino acid sequence.

Step 5: Compare the theoretical m/z value calculated in Step 4 with the actual m/z value obtained in Step 3 above, and assign the actual m/z value to a protein and an amino acid sequence thereof that have theoretical m/z values that match the actual m/z values.

Step 6: Obtain an amino acid sequence similar to the protein assigned in Step 5 above from the database.

Step 7: Among microorganisms having similar amino acid sequences obtained in Step 6 above, select a microorganism according to discrimination and classification, and calculate the theoretical m/z value of the amino acid sequence of the protein possessed by the microorganism.

Step 8: Compare the theoretical m/z values of the amino acid sequence calculated in Step 7 for each classification, and identify the protein with different theoretical m/z values for each classification as a marker for discrimination.

Effects of the Invention

According to the present invention, it is possible to identify a marker for discriminating a microorganism based on a small amount of measured data. For example, for *Salmonella,* 26 new markers could be identified in addition to markers identified in Non-Patent Document 1.

BRIEF DESCRIPTION OF THE DRAWINGS

FIG. 1 is a flow chart showing a method for identifying a marker used for discriminating a microorganism according to the present invention.

FIG. 2 is a mass spectrum of ChaB, one of the markers identified by the method of the present invention, in *S. enteritidis* and *S. typhimurium.*

MODE FOR CARRYING OUT THE INVENTION

A method for identifying a marker used for discriminating a microorganism of the present invention are described below.

Even microorganisms belong to the same genus and species as described above, they are further classified into numerous subspecies, serotypes, and strains. In addition, some species, subspecies, and serotypes are toxic to humans, and their effective therapeutic agents differ. Therefore, it is important to discriminate microorganisms by a simple and rapid method. Microorganisms to be discriminated in the present invention mainly include bacteria, actinomycetes, *Bacillus subtilis*, and fungi, for example including *Salmonella* and *Escherichia coli*, but are not limited thereto.

A marker is generally a specific characteristic of each element that is used to discriminate different elements belonging to a group. In the case of microorganisms, for example, proteins with partially different amino acid sequences in different genera, different species belonging to the same genus, or in different subspecies, serotypes, or strains belonging to the same species, are used as markers.

In the present invention, attention is paid to proteins possessed by microorganisms, and proteins capable of discriminating genera, species, subspecies, serotypes, or strains are identified based on genetic information (genome information) common to microorganisms to be discriminated. The identified protein can be used as a marker for discriminating a microorganism to be discriminated. Also, the identified marker does not necessarily have to be a marker that discriminates subspecies, serotypes, or strains, and may be a marker that discriminates only a genus or only a species depending on the purpose.

A protein used as a marker may be a protein possessed by a microorganism, and for example, intracellular proteins of a microorganism are preferably used as a marker. Examples of intracellular proteins include, but are not limited to, ribosomal proteins.

Mass spectrometry is used to identify the marker. In particular, it is preferable to use MALDI-MS that employs a soft ionization method that ionizes a macromolecule without decomposing it as much as possible. Markers are identified by mass spectrometry, using peak data for molecular weight-related ion, such as a molecule in which a proton is added to protein M which is a neutral molecule (hereinafter, may be referred to as "$[M+H]^{+}$"). At this time, as a m/z value of the protein, it is desirable to use a calculated mass obtained by translating a base sequence of each protein into an amino acid sequence. Furthermore, when calculating the calculated mass from the amino acid sequence, it is desirable to consider cleavage of a N-terminal methionine residue as a post-translational modification. Specifically, theoretical values are calculated assuming that the N-terminal methionine is cleaved when a penultimate amino acid residue is Gly, Ala, Ser, Pro, Val, Thr or Cys.

The method for identifying the marker for discriminating the microorganism of the present invention is carried out according to the following procedure as shown in the flow chart of FIG. 1

Step 1: Select a microorganism whose entire genome has been decoded from among microorganisms to be discriminated.

Step 2: Perform mass spectrometry on a protein possessed by the microorganism selected in Step 1 above to obtain molecular weight-related ion peaks such as $[M+H]^+$ based on an amino acid sequence of the protein (hereinafter, may be referred to as "molecular weight-related ion peaks").

Step 3: Obtain a m/z value of each peak is obtained as a measured value (actual measure value) from the molecular weight-related ion peaks obtained in Step 2 above (hereinafter, may be referred to as "actual m/z value").

Step 4: For the microorganism selected in Step 1 above, obtain information of the protein possessed by the microorganism and an amino acid sequence thereof from a genetic database, and calculate a theoretical m/z value of the protein from the information of the amino acid sequence (Hereinafter, may be referred to "theoretical m/z value").

Step 5: Compare the theoretical m/z value calculated in Step 4 with the actual m/z value obtained in Step 3 above, and assign the actual m/z value to a protein and an amino acid sequence thereof that have theoretical m/z values that match the actual m/z values.

Step 6: Obtain an amino acid sequence similar to the protein assigned in Step 5 above from the database.

Step 7: Among microorganisms having similar amino acid sequences obtained in Step 6 above, select a microorganism according to discrimination and classification, and calculate the theoretical m/z value of the amino acid sequence of the protein possessed by the microorganism.

Step 8: Compare the theoretical m/z values of the amino acid sequence calculated in Step 7 for each classification, and identify the protein with different theoretical m/z values for different classifications such as genus, species, subspecies, serotype, and strain as a marker for discrimination.

Usually, a microorganism has multiple identical proteins in different genera, species, subspecies, serotypes and strains, and by combining multiple m/z values of the above marker protein, the genus, species, subspecies, serotype and strain of the microorganism can be discriminated.

Each step is described in more detail below.

[Steps 1 to 3]

The Microorganism whose entire genome has been decoded selected from among microorganisms to be discriminated in Step 1 may be selected based on publicly known databases such as gene databases, such as UniProt (registered trademark, also known as The Universal Protein Resource), NCBI, and supplier information. When the microorganism whose entire genome has been decoded is selected, the microorganism is obtained, and in Step 2, mass spectrometry is performed to obtain molecular weight-related ion peaks based on the amino acid sequence of the protein. The mass spectrometry method is preferably MALDI-MS as described above. MALDI-MS obtains molecular weight-related ion peaks such as $[M+H]^+$ based on the amino acid sequence for each protein, and for each peak, in Step 3, its m/z value is obtained.

[Step 4]

On the other hand, since the entire genome of the microorganism selected in Step 1 has been decoded, the protein contained in the microorganism and its amino acid sequence are known and are usually recorded in the gene database. Therefore, it is possible to obtain the amino acid sequences of all proteins contained in the microorganism selected in Step 1 from the database and calculate the respective theoretical m/z values. Databases to be used include, for example, UniProt (registered trademark, also known as The Universal Protein Resource), NCBI, and the like.

[Step 5]

In step 5, by comparing the actual m/z value obtained in Step 3 and the theoretical m/z value calculated in Step 4, all the molecular weight-related ion peaks obtained by the mass spectrometry in Step 2 can be assigned to known proteins and their amino acid sequences.

[Step 6]

In the case of microorganisms, the protein mass may differ depending on the genus, the species, the subspecies, the serotype or the strain. This difference in mass is thought to be due to mutation of amino acids that constitute the protein. In Step 6, in order to search for amino acid sequence variants, amino acid sequences similar to the assigned protein are searched.

A protein having a similar amino acid sequence in Step 6 above can be identified by searching, for example, an existing database of microorganisms. Examples of search methods include similarity search (homology search) using databases such as UniProt and NCBI. When performing the similarity search, for example, the search is performed under the condition that the sequence similarity is 50% or more. The degree of sequence similarity may be appropriately set according to the purpose of discrimination.

[Step 7]

Since the proteins having similar amino acid sequences selected in Step 6 above include the amino acid sequences of microorganisms belonging to various genera or species, microorganisms are selected according to the discrimination and classification. For example, if the classification is species, subspecies, serotype or strain, microorganisms of the same genus as those selected in Step 1 are selected. Also, when the classification is by genus, all microorganisms are selected regardless of the genus. Then, the theoretical m/z values of the amino acid sequences of these screened microorganisms are obtained.

[Step 8]

The theoretical m/z values of the detected proteins and their amino acid sequences are obtained by mass spectrometry of the microorganisms whose entire genomes have been decoded in Steps 4 to 7. At the same time, theoretical m/z values of proteins possessed by microorganisms of the same genus and different species, for example, having amino acid sequences similar to those of microorganisms whose entire genomes have been decoded, are obtained. In Step 8, for example, comparing the theoretical m/z values based on the amino acid sequences of proteins possessed by microorganisms of the same genus and different species, when a protein with an m/z value that differs between species can be identified, the protein is identified as a marker for species discrimination. In Step 8, if multiple proteins with different m/z values can be identified, all proteins with different m/z values may be identified as markers, or among these proteins, for example, a protein with high intensity m/z value may be identified as a marker, or proteins with m/z values that differ from the m/z values of other markers by 200 ppm or more, preferably 500 ppm or more, more preferably 800 ppm or more may be identified as markers.

The markers identified by the above steps will have different theoretical m/z values for the same protein if the genera, species, subspecies or serotypes are different. That is, since each protein has a different theoretical m/z value for each genus, species, subspecies or serotype, it can be used as a marker for their discrimination. At this time, even if some of the genera, species, subspecies or serotypes have the same theoretical m/z value, they can be used as markers for discrimination when a combination of theoretical m/z values of a plurality of proteins contributes to discrimination as a whole.

Taking *Salmonella* as an example of microorganisms, the above method will be described in more detail below.

Examples of Salmonellae selected in step 1, whose entire genome have been decoded, include *Salmonella enterica* subsp. *enterica* serovar *Abaetetuba* (hereinafter, may be referred to as "*S. abaetetuba*") (strain: ATCC 35640) and *Salmonella enterica* subsp. *enterica* serovar *Typhimurium* (strain: ATCC 700720).

For example, mass spectrometry of the above *S. abaetetuba* by MALDI-MS yields molecular weight-related ion peaks such as $[M+H]^+$ based on the amino acid sequence of the protein.

When self-calibration is applied to the measured protein molecular weight-related ion peaks, more precise m/z values are obtained.

On the other hand, the genome information of *S. abaetetuba* is open to the public, and all protein names and amino acid sequence data can be obtained from, for example, the database UniProt. The m/z value of the molecular weight-related ion peaks of each protein can be calculated from the obtained amino acid sequence information. By comparing the theoretical m/z value calculated in this way with the actually measured m/z value of the molecular weight-related ion peaks of the protein previously measured, the m/z values of the measured protein molecular weight-related ion peaks can be assigned to proteins and amino acid sequences.

Since a number of molecular weight-related ion peaks actually measured for *S. abaetetuba* is enormous, the attributed molecular weight-related ion peaks may be appropriately selected. For example, peaks with m/z values in the range of 2000 to 20000, preferably 3000 to 15000 may be selected and assigned. Also, peaks with an S/N of 2 or more, preferably 3 or more may be selected and assigned.

Theoretical m/z values of similar amino acid sequences can be obtained by performing the similarity search using, for example, UniProt, on the proteins assigned above. By selecting amino acid sequences belonging to *Salmonella* and their proteins from among them, each species, each subspecies, each serotype or each strain of *Salmonella* and its theoretical m/z values can be obtained.

By comparing the theoretical m/z values for each *Salmonella* species, subspecies and serotype obtained as described above, proteins that exhibit different m/z values for different species, subspecies, serotypes or strains can be selected as markers.

Whether or not the marker selected by the above method is correct can be confirmed, for example, by the following procedure. First, a microorganism whose species, subspecies, or serotype is known is subjected to mass spectrometry by MALDI-MS, and the m/z value for the molecular weight-related ion peaks of the protein obtained by actual measurement is determined in the same manner as described above. It can be confirmed by whether or not the protein selected as a marker is detected at the theoretical m/z value as a result of mass spectrometry.

Taking the above *Salmonella* as an example, first, a plurality of Salmonellae whose serotypes are known are subjected to mass spectrometry by MALDI-MS, and the m/z value for the molecular weight-related ion peaks of the protein obtained by actual measurement is determined in the same manner as described above. As a result of mass spectrometry, it can be confirmed whether or not the protein selected as a marker is reproducibly detected according to the theoretical m/z value based on the amino acid sequence of the protein in the above serotype.

Usually, when subspecies of a microorganism is known, the species is known, and when the serotype is known, the species and subspecies are known. On the other hand, even if the species is known, the subspecies or serotype may not be known.

Therefore, in the above confirmation method, for example, in order to confirm the marker for discriminating species, it is necessary to use microorganisms whose species, or species and subspecies, or species, subspecies and serotypes are known. In addition, in order to confirm the marker for identifying species and subspecies, it is necessary to use microorganisms whose species and subspecies, or species, subspecies and serotypes are known.

The microorganism to be discriminated is discriminated using the marker identified by the method described above. As a discrimination method, for example, a method of performing mass spectrometry on the microorganism to be discriminated can be adopted, similar to the method for identifying the marker. In particular, it is preferable to use MALDI-MS that employs a soft ionization method that ionizes the macromolecule without decomposing it as much as possible.

The microorganism to be discriminated is subjected to mass spectrometry to obtain the molecular weight-related ion peaks of the protein. The presence or absence of the theoretical m/z value assigned to the protein identified as the marker is confirmed from the resulting molecular weight-related ion peaks. Alternatively, it is confirmed at which theoretical m/z value the marker protein peak is detected. If the existence of a peak in the theoretical m/z value assigned to the protein identified as the marker is confirmed in the microorganism to be discriminated, the species, subspecies, serotypes, etc. having the protein are identified. Alternatively, the species, subspecies, serotype, or the like of the microorganism to be discriminated is discriminated based on the m/z value of the peak of the marker protein.

As described above, by selecting the marker that can be used to discriminate the microorganism in advance, mass spectrometry of the microorganism to be discriminated allows discrimination of the genus, species, subspecies or serotype to which the microorganism belongs. In addition, it is not necessary to separately analyze all possible genera, species, subspecies and serotypes and compare them with the microorganism to be discriminated, and only the microorganism to be discriminated needs to be analyzed.

The selected marker facilitates discrimination of genus, species, subspecies, and serotypes, and allows convenient and rapid identification of genus, species, subspecies, and serotypes of a microorganism. In addition, identifying the markers for each genus, species, subspecies, and serotype, a database consisting of at least one of the identified markers together with its theoretical m/z value and at least one of the genus, species, subspecies or serotype can also be constructed. For example, the markers that can discriminate subspecies are identified, and a database of each subspecies and its markers can be constructed. By constructing such a database, it is possible to immediately discriminate the genus, species, subspecies or serotype of a microorganism to be discriminated from the results of mass spectrometry. In addition, the marker selection method of the present invention only needs to analyze a microorganism whose entire genomes has been decoded, it is possible to reduce the number of actual measurements of the microorganism that are pathogenic to humans, and it is also useful from the viewpoint of the safety and labor of inspectors.

EXAMPLES

Hereinafter, the present invention will be specifically described with reference to examples, but the present invention is not limited to these examples.

*Salmonella* was used as a test sample as a microorganism, and markers that can be used to identify species, subspecies, and serotypes of *Salmonella* were identified.

The test sample was subjected to mass spectrometry by MALDI-MS. The apparatus used for MALDI-MS is AXIMA (registered trademark) Performance manufactured by Shimadzu Corporation, and the measurement conditions are as follows.

[Mass Spectrometry Conditions]

Equipment: Shimadzu AXIMA (registered trademark) Performance

Conditions: positive mode, Lin mode, Raster analysis.

[Procedure]

*Salmonella* markers were identified and confirmed by the following procedures (steps) 1 to 9.

1. A strain of *Salmonella enterica* subsp. *enterica* serovar *Abaetetuba* (hereinafter referred to as "*S. abaetetuba*"): ATCC 35640 was selected as a whole genome decoded strain of *Salmonella* and cultured on an LB agar medium at a temperature of 37° C. for 20 hours. Similarly, each strain of two *Salmonella* serotype: *S. enteritidis* (strains: GTC00131, GTC09491, HyogoSE11002, HyogoSE12001) and *S. typhimurium* (strains: NBRC14210, NBRC15181, NBRC12529, NBRC13245) was cultured on LB agar medium at 37° C. for 20 hours.

2. As a matrix solution, the following sinapinic acid (manufactured by Wako Corporation, hereinafter referred to as "SA") solution was prepared and used in the following steps.

SA-1: SA 25 mg/mL ethanol (hereinafter referred to as "EtOH") solution

SA-2: An aqueous solution consisting of SA 25 mg/mL methylene diphosphoric acid (manufactured by Sigma-Aldrich Corporation, hereinafter referred to as "MDPNA") 1% by weight, n-decyl-β-D-maltopyranoside (manufactured by Sigma-Aldrich Corporation, hereinafter referred to as "DMP") 1 mM, trifluoroacetic acid (manufactured by Wako Corporation, trifluoroacetic acid, hereinafter referred to as "TFA") 0.6% by weight, and acetonitrile (manufactured by Wako Corporation, acetonitrile, hereinafter referred to as "ACN") 50% by weight.

plate was inserted into MALDI-MS and measured by raster analysis in positive, Lin mode. The number of n was set to 4. After measurement, *Salmonella* self-calibration was applied and the resulting mass spectra were evaluated to confirm the m/z values of the detected protein peaks.

5. All amino acid sequences and protein names were obtained from the public genetic information of *S. abaetetuba*, a whole genome decoded strain. From this amino acid sequence information, a theoretical m/z value based on the amino acid sequence of each protein was calculated.

6. For the proteins obtained in Step 5 above, among the mass spectrum peaks obtained in the above Step 4, proteins assigned to peaks in which the m/z value is in the range from 3000 to 20000, peak signal/noise ratio (S/N) is 3 or more, mass accuracy is within 500 ppm, n is detected 3 or more times out of 4, and which do not have two or more approximations of the theoretical m/z value of the protein obtained in Step 5 for one peak were selected.

7. For each protein in Step 6 above, similar amino acid sequence information was searched by similarity search of published gene information (sequence similarity of 50% or more) and a theoretical m/z value for each strain of *Salmonella* was obtained along with species, subspecies and serotype information.

8. The theoretical m/z values obtained in Step 7 above were compared for each *Salmonella* species, subspecies, and serotype and proteins with different m/z values for different species, subspecies, and serotypes were identified as markers.

[Result]

First, in the mass spectra of *S. enteritidis* (strains: GTC00131, GTC09491, HyogoSE11002, HyogoSE12001) and *S. typhimurium* (strains: NBRC14210, NBRC15181, NBRC12529, NBRC13245), table 1 summarizes the detection status of representative peaks among the major proteins selected in the same manner as in Step 6 above. As a result, the measured data almost reflected the m/z value information of the protein calculated from the gene information.

TABLE 1

Peak detection rate (%) of major proteins of *S. Enteritidis* and *S. Typhimurium*

| | Protein | | | | | | | | | | |
|---|---|---|---|---|---|---|---|---|---|---|---|
| | S15 | S22 | YjbJ | ChaB | YeiS | YcaR | SsaG | ZapB | YgaM | RaiA | IraP |
| *S. Enteritidis* | 100 | 75 | 100 | 100 | 100 | 100 | 100 | 100 | 100 | 100 | 100 |
| *S. Typhimurium* | 100 | 50 | 100 | 100 | 50 | 100 | 100 | 100 | 100 | 100 | 100 |

| | Protein | | | | | | | | | |
|---|---|---|---|---|---|---|---|---|---|---|
| | HU2 | BcsR | Nucleptidyl transferase | IHFa | CheY | rpoZ | YifE | IHFb | YeeX | HU-1 |
| *S. Enteritidis* | 100 | 75 | 100 | 100 | 100 | 100 | 100 | 100 | 100 | 100 |
| *S. Typhimurium* | 100 | 50 | 100 | 100 | 100 | 100 | 100 | 100 | 100 | 100 |

3. About 1 mg of *Salmonella* from Step 1 above with a microbalance was weigh, the SA-2 solution prepared in Step 2 was added to the *Salmonella*, and the *Salmonella* was suspended with a needle so that the concentration of *Salmonella* was 1 mg/0.075 mL ($1\times10^7$ cells/μL). After that, ultrasonic waves were applied for 1 minute, and the resulting suspension was centrifuged at 12000 rpm for 5 minutes.

4. 0.5 μL of the SA-1 solution prepared in Step 2 above was dropped onto a MALDI plate to precoat it. After that, 1 μL of the supernatant after centrifugation in Step 3 above was dropped onto the precoated wells. After air-drying, the The detection rate was obtained as follows.

Measurements were performed four times for each strain for each serotype, and strains in which the protein was detected were determined when the protein was detected three times or more with an S/N>3 and a mass accuracy of 500 ppm or less. The detection rate was obtained by dividing the number of strains detected by the total number of strains measured. For example, the detection rate is 100% when protein is detected in 4 out of 4 strains, and the detection rate is 75% in 3 out of 4 strains.

As can be seen from Table 1, peaks are detected almost as theoretical values, except for some. The reason for the low detection rate for some proteins was the low sensitivity of protein peaks. From this result, it was confirmed that it is possible to predict the m/z value of the detected peak from the genetic information. Thus, it was thought that marker proteins could be predicted based on genetic information.

Next, in the above Step 8, the theoretical m/z values are compared for each *Salmonella* species, subspecies, and serotype, and the following 26 proteins showing different m/z values for each species, subspecies, and serotype were identified as the marker proteins.

S22, YcaR, L35, BcsR, SsaG,
Nucleotidyl transferase, YibJ, OadG,
ChaB, ZapB, HU-1, YeiS, HU-2, IraP, S15,
rpoZ, IHFb, IHFa, YgaM, RaiA, YifE,
YeeX, Endolysin, RNaseP, CheY, S5

For example, for the protein ChaB identified as a marker in Step 8, the measured peaks of two *Salmonella* serotypes (*S. enteritidis* and *S. typhimurium*) are shown in FIG. 2, and the theoretical m/z values are shown in Table 2. As can be seen from FIG. 2 and Table 2, it was confirmed that two serotypes (*S. enteritidis* and *S. typhimurium*) could be discriminated by the protein, ChaB, identified as a marker.

TABLE 2

Theoretical m/z values of ChaB for *S. Enteritidis* and *S. Typhimurium*

| | Marker candidate (theoretical m/z values) ChaB |
|---|---|
| *S. Enteritidis* | 8848 |
| | 8849 |
| | 8851 |
| *S. Typhimurium* | 8819 |
| | 8849 |
| | 9971 |

Furthermore, Tables 3, 5, and 7 show the results of summarizing the theoretical m/z values of species, subspecies, and serotypes of the 26 types of the proteins identified as markers above. In addition, Tables 4, 6, and 8 show the results of summarizing the theoretical m/z values of the 12 types of marker proteins for *Salmonella* serotype discrimination reported in Non-Patent Document 1.

TABLE 3

Examples of theoretical m/z values of 26 novel marker proteins for discrimination of *Salmonella* species

| | S15 | S22 | YeiS | YcaR | YgaM | RaiA | IraP | HU-2 | BcsR |
|---|---|---|---|---|---|---|---|---|---|
| *S. bongori* | 10068 | 5356 | 9377 | 6873 | 11916 | 11645 | 9732 | 9522 | 7064 |
| | 10109 | | 9407 | | | 12549 | 9790 | | |
| | | | 9622 | | | | 10826 | | |
| *S. enterica* | 10049 | 5215 | 9227 | 6840 | 11886 | 12522 | 9772 | 8765 | 7053 |
| | 10065 | 5340 | 9412 | 6844 | 11902 | 12535 | 9786 | 8937 | 7060 |
| | 10068 | 5350 | 9530 | 6856 | 11917 | 12551 | 9856 | 9506 | 7063 |
| | 10080 | 5357 | 9543 | 6859 | 11948 | 12565 | 10026 | 9522 | 7093 |
| | 10109 | 5369 | 9634 | 6873 | 11960 | 12623 | 11482 | 9536 | 7560 |
| | 10167 | etc. | etc. | etc. | etc. | etc. | etc. | etc. | etc. |

| | IHFa | CheY | rpoZ | YifE | IHFb | YeeX | HU-1 | Endolysin |
|---|---|---|---|---|---|---|---|---|
| *S. bongori* | 11238 | 13995 | 10107 | 12904 | 10491 | 13060 | 9241 | 14303 |
| | | | | 12948 | | | | |
| *S. enterica* | 11220 | 13953 | 8838 | 12832 | 10419 | 13008 | 9188 | 13100 |
| | 11238 | 13995 | 10088 | 12933 | 10461 | 13044 | 9241 | 13434 |
| | 11250 | 14025 | 10093 | 12948 | 10477 | 13059 | 9269 | 13484 |
| | 11254 | 14067 | 10107 | 12962 | 10491 | 13073 | 9327 | 13459 |
| | 11310 | 15038 | 10449 | 12974 | 10519 | 13102 | 9352 | 13506 |
| | etc. | etc. | etc. | etc. | etc. | etc. | etc. | etc. |

Table 3 shows the theoretical m/z values of representative 17 types of the 26 types of proteins identified above as markers (S15, S22, YeiS, YcaR, YgaM, RaiA, IraP, HU2, BcsR, IHFa, CheY, rpoZ, YifE, IHFb, YeeX, HU1, Endolysin) for two *Salmonella* species (*S. bongori, S. enterica*). Underlined numbers in the table indicate theoretical m/z values confirmed for that species only. However, the m/z values within 500 ppm between species are not underlined. When there are multiple m/z values, values other than the representative value are indicated as "etc.". In this case, as representative values, representative m/z values that differ between species and, if there are approximate m/z values between species, those m/z values are shown preferentially.

When a peak is confirmed at the underlined m/z value, it indicates that the species may be identified only by that peak. In addition, even if it is difficult to discriminate by a single protein, it can be identified by confirming the m/z values of multiple proteins. In addition, by combining with the detection status of the m/z values of known marker proteins as shown in Table 4 below, there is a possibility that discrimination that is difficult with known marker proteins alone can be performed.

TABLE 4

Examples of theoretical m/z values of 12 known marker proteins for discrimination of *Salmonella* species

| | YibT | YaiA | PPlase | L17 | L25 | Gns |
|---|---|---|---|---|---|---|
| *S. bongori* | 7959 | 7109 | 10168 | 14453 | 10569 | 6497 |
| | | | | | 10583 | |
| | 7954 | 7101 | 10154 | 14382 | 10542 | 6483 |
| | 7962 | 7109 | 10168 | 14396 | 10556 | 6491 |

TABLE 4-continued

Examples of theoretical m/z values of 12 known marker proteins for discrimination of *Salmonella* species

| | YibT | YaiA | PPlase | L17 | L25 | Gns |
|---|---|---|---|---|---|---|
| *S. enterica* | 7966 | 7111 | 10180 | 14437 | 10569 | 6497 |
| | 7993 | 7127 | 10193 | 14453 | 10639 | 6508 |
| | 8011 | 7139 | 10198 | 14481 | 10648 | 6512 |
| | etc. | etc. | etc. | etc. | etc. | etc. |

Table 4 shows the theoretical m/z values of representative 6 types of the 12 types of known marker proteins for serotype discrimination reported in Non-Patent Document 1 for two *Salmonella* species (*S. bongori, S. enterica*). Underlined numbers in the table indicate theoretical m/z values confirmed for that species only. However, the m/z values within 500 ppm between species are not underlined. When there are multiple m/z values, values other than the representative value are indicated as "etc.". In this case, as representative values, representative m/z values that differ between species and, if there are approximate m/z values between species, those m/z values are shown preferentially.

The 6 types of proteins exemplified are 6 out of 12 markers for serotype discrimination reported in Non-Patent Document 1 and are not known as markers for discrimination of the species exemplified in Table 4.

When a peak is confirmed at the underlined m/z value in Table 4, it indicates that the species may be identified only by that peak. In addition, even if it is difficult to discriminate by a single protein, it can be identified by confirming the m/z values of multiple proteins. In addition, by combining with the detection status of the m/z values of the novel marker proteins as shown in Table 3 above, there is a possibility that discrimination that is difficult with known marker proteins alone can be performed.

TABLE 5

Examples of theoretical m/z values of 26 novel marker proteins for discrimination of *Salmonella* subspecies

| genus | species | subspecies | ChaB | YeiS | SsaG | IraP | BcsR | Eodolysin | |
|---|---|---|---|---|---|---|---|---|---|
| *Salmonella* | *enterica* | *houtenae* | 8832 | 9414 | 7953 | — | 7645 | 13052 | |
| | | | | 9659 | | | | 13151 | |
| | | *salamae* | — | 9523 | 7991 | 9856 | 7063 | 12443 | |
| | | | | 9657 | 8024 | 9946 | | 13100 | |
| | | | | 9661 | | 9955 | | 13130 | |
| | | | | 9678 | | | | 13342 | |
| | | | | 9669 | | | | 13372 | |
| | | | | 9690 | | | | 13378 | |
| | | *indica* | — | 9414 | 7991 | 9786 | 7063 | 13454 | |
| | | | | 9661 | | | | | |
| | | *diarizonae* | 8775 | 9647 | 8009 | — | 7063 | 12546 | |
| | | | | 9676 | 8010 | | 7079 | | |
| | | | | 9687 | 8040 | | 7614 | | |
| | | | | 9690 | | | | | |
| | | | | 9692 | | | | | |
| | | *arizonae* | 8778 | 9431 | 7997 | 9856 | 7063 | 12546 | |
| | | | 8819 | 9527 | 8010 | 9955 | 7093 | 13011 | |
| | | | 8826 | 9543 | | | | | |
| | | | 9971 | 9772 | | | | | |
| | | | | 9786 | | | | | |
| | | *enterica* | 8766 | 9312 | 7927 | 9847 | 7063 | 12443 | 13375 |
| | | | 8775 | 9412 | 7945 | 9856 | 7093 | 12546 | 33386 |
| | | | 8803 | 9424 | 7953 | 9884 | 7555 | 12607 | 13434 |
| | | | 8819 | 9431 | 7963 | 9903 | 7587 | 13011 | 13448 |
| | | | 8826 | 9442 | 7973 | 9942 | 7603 | 13952 | 13459 |
| | | | 8832 | 9456 | 7991 | 9955 | 7614 | 13130 | |
| | | | 8863 | 9530 | 7997 | 9967 | 7628 | 13309 | |
| | | | 9911 | 9533 | 8010 | 9969 | 7645 | 13317 | |
| | | | 9971 | 9585 | 8024 | 9983 | 7831 | 13361 | |
| | | | etc. | etc. | etc. | etc. | etc. | | etc. |

Table 5 shows the theoretical m/z values of representative 6 types (ChaB, YeiS, SsaG, IraP, BcsR, Endolysin) of the 26 types of the novel marker proteins for six subspecies of *Salmonella enterica* (*houtenae, salamae, indica, diarizonae, arizonae, enterica*). A hyphen in the table indicates that there is no description in the database. Underlined numbers in the table indicate theoretical m/z values confirmed for that subspecies only. However, the m/z values within 500 ppm between species are not underlined. When there are multiple m/z values, values other than the representative value are indicated as "etc.". In this case, as representative values, representative m/z values that differ between species and, if there are approximate m/z values between species, those m/z values are shown preferentially.

When a peak is confirmed at the underlined m/z value, it indicates that the species may be identified only by that peak. In addition, even if it is difficult to discriminate by a single protein, it can be identified by confirming the m/z values of multiple proteins. In addition, by combining with the detection status of the m/z values of known marker proteins as shown in Table 6 below, there is a possibility that discrimination that is difficult with known marker proteins alone can be performed.

TABLE 6

Examples of theoretical m/z values of 12 known market proteins for discrimination of *Salmonella* subspecies

| genus | species | subspecies | YibT | L15 | YaiA | Gns |
|---|---|---|---|---|---|---|
| *Salmonella* | *enterica* | *houtenae* | — | 14967 | 7067 | 6496 |
| | | | | 14995 | 7079 | 6509 |
| | | *salamae* | 7863 | 14067 | 7081 | 6494 |
| | | | | | | 6517 |
| | | *indica* | 7993 | 14985 | 7081 | 6491 |
| | | *diarizonae* | 7901 | 14807 | 7099 | 6464 |
| | | | 7966 | | 7111 | 6494 |
| | | | 7992 | | | |
| | | *arizonae* | 7861 | 14967 | 7081 | 6452 |
| | | | 7954 | | | 6480 |
| | | | 7956 | | | 6508 |
| | | | 7993 | | | |
| | | | 8062 | | | |
| | | *enterica* | 7863 | 14948 | 7081 | 6411 |
| | | | 7876 | 14953 | 7085 | 6425 |
| | | | 7892 | 14967 | 7097 | 6452 |

TABLE 6-continued

Examples of theoretical m/z values of 12 known market proteins for discrimination of *Salmonella* subspecies

| genus | species | subspecies | YibT | L15 | YaiA | Gns |
|---|---|---|---|---|---|---|
| | | | 7935 | 14981 | 7099 | 6460 |
| | | | 7966 | 15009 | 7109 | 6480 |
| | | | 7983 | | 7110 | 6494 |
| | | | 7993 | | 7111 | 6494 |
| | | | 8023 | | 7127 | 6508 |
| | | | 8066 | | 7139 | 6512 |
| | | | etc. | | 7151 | 6517 |
| | | | | | 7157 | 6524 |
| | | | | | | 6542 |
| | | | | | | etc. |

Table 6 shows the theoretical m/z values of representative 4 types (YibT, L15, YaiA, Gns) of the 12 types of known marker proteins for serotype discrimination reported in Non-Patent Document 1 for six subspecies of *Salmonella enterica* (*houtenae, salamae, indica, diarizonae, arizonae, enterica*). A hyphen in the table indicates that there is no description in the database. Underlined numbers in the table indicate theoretical m/z values confirmed for that subspecies only. However, the m/z values within 500 ppm between species are not underlined. When there are multiple m/z values, values other than the representative value are indicated as "etc.". In this case, as representative values, representative m/z values that differ between species and, if there are approximate m/z values between species, those m/z values are shown preferentially.

The 4 types of proteins exemplified are 4 out of 12 markers for serotype discrimination reported in Non-Patent Document 1 and are not known as markers for discrimination of the subspecies exemplified in Table 6.

When a peak is confirmed at the underlined m/z value, it indicates that the species may be identified only by that peak. In addition, even if it is difficult to discriminate by a single protein, it can be identified by confirming the m/z values of multiple proteins.

In addition, by combining with the detection status of the m/z values of the novel marker proteins as shown in Table 5 above, there is a possibility that discrimination that is difficult with known marker proteins alone can be performed.

TABLE 7

Examples of theoretical m/z values of 26 novel marker proteins for discrimination of *Salmonella* serotype

| genus | species | subspecies | serotype | YjbJ | ChaB | YeiS | SsaG | YgaM | RaiA | Endolysin |
|---|---|---|---|---|---|---|---|---|---|---|
| *Salmonella* | *enterica* | *enterica* | Adelaide | 8460 | 9971 | 9442 | 7991 | 11848 | 15874 | 13389 |
| | | | Agama | 8329 | 8819 | 9687 | 7945 | 11848 | 12522 | 13433 |
| | | | Agona | 8329 | 8819 | 9687 | 7945 | 11857 | 12522 | 13389 |
| | | | Alachua | 8460 | 7851 | 9873 | 7945 | 11848 | 12421 | 13375 |
| | | | Albany | 8329 | 8819 | 9687 | 7945 | 11848 | 12522 | 13389 |
| | | | Altona | 8329 | 8819 | 9687 | 7945 | 11857 | 12522 | 13375 |
| | | | Anatum | 8329 | 8819 | 9687 | 7945 | 11857 | 12522 | 13375 |
| | | | | | | | | 11848 | | 13389 |
| | | | Bareilly | 8329 | 8819 | 9687 | 7945 | 11848 | 12522 | 13357 |
| | | | Berta | 8329 | 8847 | 9687 | 7945 | 11857 | 12522 | 13357 |
| | | | | | 8848 | | | 11848 | | 13375 |
| | | | Bovismorbificans | 8460 | 8819 | 9442 | 7945 | 11848 | 12522 | 13357 |
| | | | Braenderup | 8329 | 8819 | 9687 | 7945 | 11848 | 12522 | 13357 |
| | | | Brancaster | 8329 | 8819 | 9687 | 7927 | 11857 | 12522 | 13375 |
| | | | Bredeney | 8329 | 8819 | 9687 | 7945 | 11848 | 13522 | 13375 |
| | | | Cerro | 8329 | — | 9687 | 7991 | 11848 | 12332 | 13366 |

Table 7 shows the theoretical m/z values of representative 7 types (YjbJ, ChaB, YeiS, SsaG, YgaM, RaiA, Endolysin) of the 26 types of the novel marker proteins for fourteen serotypes of *Salmonella enterica* subsp. *enterica* (*Adelaide, Agama, Agona, Alachua, Albany, Altona, Anatum, Barreilly, Berta, Bovismorbificans, Braenderup, Brancaster, Bredeney, Cerro*). A hyphen in the table indicates that there is no description in the database. It can be seen that there is a possibility of discrimination by combining the m/z values of multiple proteins. In addition, by combining with the m/z value detection status of known marker proteins as shown in Table 8 below, there is a possibility that discrimination that was difficult with known marker proteins alone can be performed.

TABLE 8

Examples of theoretical m/z values of known marker proteins for discrimination of *Salmonella* serotype

| genus | species | subspecies | serotype | SodA | YibT | L15 | PPlase | L25 | Gns |
|---|---|---|---|---|---|---|---|---|---|
| *Salmonella* | *enterica* | *enterica* | Adelaide | 22977 | 8023 | 14967 | 10198 | 10528 | 6512 |
| | | | Agama | 22992 | 7993 | 14967 | 10198 | 10542 | 6512 |
| | | | Agona | 22977 | 7993 | 14967 | 10180 | 10542 | 6484 |
| | | | Alachua | 22977 | 7993 | 14967 | 9868 | 10542 | 7526 |
| | | | Albany | 22977 | 7993 | 14967 | — | — | — |
| | | | Altona | 22977 | 7993 | 14948 | 10198 | 10542 | 6484 |
| | | | Anatum | 22977 | 7993 | 14967 | 10198 | 10542 | 6484 |
| | | | Bareilly | 22977 | 7993 | 14967 | 10188 | 10528 | 6484 |
| | | | Berta | 22990 | 7966 | 14967 | — | — | — |
| | | | | 23011 | 7993 | | | | |
| | | | Bovismorbificans | 23005 | 7993 | 14967 | 10198 | 10542 | 6484 |
| | | | Braenderup | 22963 | 7993 | 14967 | 10198 | 10528 | 6484 |
| | | | Brancaster | 23005 | 8023 | 14967 | — | — | — |
| | | | Bredeney | 22949 | — | 14967 | — | — | — |
| | | | Cerro | 22977 | 7993 | 14967 | 10198 | 10542 | 6484 |

Table 8 shows the theoretical m/z values of representative 6 types (SodA, YibT, L15, PPLase, L25, Gns) of the 14 types of the novel known marker proteins for fourteen serotypes of *Salmonella enterica* subsp. *enterica* (Adelaide, Agama, Agona, Alachua, Albany, Altona, Anatum, Barreilly, Berta, Bovismorbificans, Braenderup, Brancaster, Bredeney, Cerro). A hyphen in the table indicates that there is no description in the database. It can be seen that there is a possibility of discrimination by combining the m/z values of multiple proteins. In addition, since SodA is a high-mass protein, it has low sensitivity compared to other proteins, and the shape of the peak observed in the high-mass region tends to change, so that it is known that the accuracy of the m/z value tends to decrease.

The 6 types of proteins exemplified are 6 out of 12 markers for serotype discrimination of 22 types of serotypes reported in Non-Patent Document 1, and strictly speaking, it is not known to be effective as a discrimination marker for serotypes other than 22 types. In Table 8, all serotypes other than S. Altona and S. Braenderup are serotypes other than 22 types of serotypes.

In addition, by combining the m/z value detection status of novel marker proteins as shown in Table 7, it may be possible to make discrimination that were difficult with known marker proteins alone.

From the results in Tables 3 to 8, it was found that the 26 types of novel marker proteins confirmed by this protocol using genetic information are effective in discriminating *Salmonella* species, subspecies, and serotypes. Further, it was suggested that these marker proteins may enable discrimination that is difficult with known marker proteins alone. In addition, the method for identifying the marker for discriminating the microorganism of the present invention can identify markers for more species, subspecies, and serotypes by using genetic information.

From the above results, it was found that it is possible to predict actual measurement data from genetic information, and that the marker that discriminates the microorganism can be identified by comparing theoretical m/z values obtained from genetic information. In particular, the method for identifying the marker for discriminating the microorganism of the present invention utilizes the m/z values of detection peaks obtained by performing mass spectrometry once for *Salmonella*, for which whole genome information is known. That is, by predicting actual measurement data such as different species from genetic information using one measurement data and comparing the theoretical values from genetic information, it is possible to identify the marker that is effective in discriminating *Salmonella* species, subspecies and serotypes.

[Aspect]

It will be understood by those skilled in the art that the exemplary embodiments described above are specific examples of the following aspects.

[1] A method for identifying a marker for discriminating a microorganism, comprising steps 1 to 8 below.

Step 1: Select a microorganism whose entire genome has been decoded.

Step 2: Perform mass spectrometry on protein possessed by the microorganism selected in Step 1 above to obtain molecular weight-related ion peaks of the protein.

Step 3: Obtain an actual m/z value of each peak from the molecular weight-related ion peaks obtained in Step 2 above.

Step 4: For the microorganism selected in Step 1 above, obtain information of the protein possessed by the microorganism and an amino acid sequence thereof from a genetic database, and calculate a theoretical m/z value of the protein from the information of the amino acid sequence.

Step 5: Compare the theoretical m/z value calculated in Step 4 with the actual m/z value obtained in Step 3 above, and assign the actual m/z value to a protein and an amino acid sequence thereof that have theoretical m/z values that match the actual m/z values.

Step 6: Obtain an amino acid sequence similar to the protein assigned in Step 4-5 above from the database.

Step 7: Among microorganisms having similar amino acid sequences obtained in Step 6 above, select a microorganism according to discrimination and classification, and calculate the theoretical m/z value of the amino acid sequence of the protein possessed by the microorganism.

Step 8: Compare the theoretical m/z values of the amino acid sequence calculated in Step 7 for each classification, and identify the protein with different theoretical m/z values for each classification as a marker for discrimination.

According to the above invention [1], there is provided a method for identifying the marker for discriminating the microorganism based on a small amount of measured data.

[2] The method for identifying the marker for discriminating the microorganism according to [1] above, wherein the mass spectrometry is MALDI-MS.

According to the above invention [2], an analysis result can be obtained in a short period of time using a very small amount of a microbial sample, and continuous analysis of many specimens is also facilitated.

[3] The method for identifying the marker for discriminating the microorganism according to [1] or [2] above, wherein the microorganism is *Salmonella*.

According to the above invention [3], a *Salmonella* discrimination marker can be identified.

[4] A method for discriminating a microorganism using the marker for discriminating the microorganism identified by the method described in [1] above.

According to the above invention [4], the microorganism can be rapidly identified with a small number of actual measurements.

[5] The method for discriminating the microorganism according to [4] above, wherein the microorganism is *Salmonella*.

According to the above invention [5], *Salmonella* can be rapidly discriminated.

[6] A database comprising the marker for discriminating the microorganism identified by the method described in [1] above and the theoretical m/z value thereof, and at least one selected from the group consisting of microorganism genera, species, subspecies, serotypes and strains corresponding to the marker.

By using the above invention [6], the microorganism can be easily identified.

What is claimed is:

1. A method for identifying a marker for discriminating a microorganism, comprising steps 1 to 8 below:

step 1: select a microorganism whose entire genome has been decoded, step 2: perform mass spectrometry on protein possessed by the microorganism selected in step 1 above to obtain molecular weight-related ion peaks of the protein, step 3: obtain an actual m/z value of each peak from the molecular weight-related ion peaks obtained in step above, step 4: for the microorganism selected in step 1 above, obtain protein information of the protein possessed by the microorganism and amino acid sequence information thereof from a genetic database, and calculate a theoretical m/z value of the protein from the obtained amino acid sequence information, step 5: compare the theoretical m/z value calculated in step with the actual m/z value obtained in step 3 above, and assign the actual m/z value to a protein and an amino acid sequence thereof that have theoretical m/z values that match the actual m/z values, step 6: obtain an amino acid sequence information similar to the protein assigned in step 5 above from the genetic database, step 7: among microorganisms having similar amino acid sequences based on the amino acid sequence information obtained in step 6 above, select a microorganism according to discrimination and classification, and calculate the theoretical m/z value of the amino acid sequence of the protein possessed by the microorganism, and step 8: compare the theoretical m/z values of the amino acid sequence calculated in step 7 for each classification, and identify the protein with different theoretical m/z values for each classification as a marker for discrimination.

2. The method for identifying the marker for discriminating the microorganism as claimed in claim 1, wherein the mass spectrometry is MALDI-MS.

3. The method for identifying the marker for discriminating the microorganism as claimed in claim 1, wherein the microorganism is *Salmonella*.

4. A method for discriminating a microorganism using the marker for discriminating the microorganism identified by the method as claimed in claim 1.

5. The method for discriminating the microorganism as claimed in claim 4, wherein the microorganism is *Salmonella*.

6. A method for constructing a database including a marker for discriminating a microorganism and a theoretical m/z value thereof, and at least one selected from the group consisting of genera, species, subspecies, serotypes and strains of a microorganism corresponding to the marker, the method comprising:

identifying the marker for discriminating the microorganism by the method as claimed in claim 1; and constructing the database comprising the marker for discriminating the microorganism and the theoretical m/z value thereof, and at least one selected from the group consisting of genera, species, subspecies, serotypes and strains of the microorganism corresponding to the marker.

* * * * *